United States Patent [19]

Bishop et al.

[11] 4,400,550

[45] Aug. 23, 1983

[54] SYNTHESIS OF THE NAVEL ORANGE WORM PHEROMONE (Z,Z)-11,13-HEXADECADIENAL

[75] Inventors: Clyde E. Bishop, Dublin; Gary W. Morrow, Columbus, both of Ohio

[73] Assignee: Albany International Corp., Albany, N.Y.

[21] Appl. No.: 348,501

[22] Filed: Feb. 12, 1982

[51] Int. Cl.³ ............................................. C07C 47/21
[52] U.S. Cl. ................................... 568/486; 568/460; 570/220; 570/216
[58] Field of Search ..................... 568/486, 448, 460; 570/216, 219, 220, 221

[56] References Cited

U.S. PATENT DOCUMENTS

| | | | |
|---|---|---|---|
| 3,567,794 | 3/1971 | Eberly | 570/220 |
| 3,691,240 | 9/1972 | Kircher et al. | 570/220 |
| 3,821,421 | 6/1974 | Behemann et al. | 568/486 |
| 3,823,195 | 7/1974 | Smith | 570/220 |
| 3,865,886 | 2/1975 | Schindler et al. | 570/220 |
| 3,920,755 | 11/1975 | Schreiber et al. | 568/486 |
| 3,929,915 | 12/1975 | Evers et al. | 568/486 |
| 3,978,092 | 8/1976 | Ichikawa et al. | 568/486 |
| 4,107,217 | 8/1978 | Schreiber et al. | 568/486 |
| 4,124,644 | 11/1978 | Sprecker et al. | 568/486 |
| 4,209,644 | 6/1980 | Ichikawa et al. | 568/486 |
| 4,288,636 | 9/1981 | Nissen et al. | 568/486 |

*Primary Examiner*—Werren B. Lone
*Attorney, Agent, or Firm*—Kane, Dalsimer, Kane, Sullivan & Kurucz

[57] ABSTRACT

A process for the synthesis of (Z,Z)-11-13-hexadecadienal is disclosed, starting with undecylenic alcohol.

3 Claims, No Drawings

SYNTHESIS OF THE NAVEL ORANGE WORM PHEROMONE (Z,Z)-11,13-HEXADECADIENAL

BACKGROUND OF THE INVENTION

1. Field of the Invention

The invention relates to the chemical synthesis of conjugated diene hydrocarbons and more particularly relates to the synthesis of a (Z,Z) conjugated diene aldehyde.

2. Brief Description of the Prior Art

P. E. Sonnet and R. R. Heath J. Chem. Ecol., 6 (1), 221-28 (1980) describe a straightforward approach to obtaining the conjugated diene system through borane reduction of the appropriate diyne obtained from Chodkiewicz-Cadiot coupling of the appropriate acetylenes. This process suffers, however, from two weaknesses; it utilizes chromium oxidation to generate the aldehyde and two equivalents of expensive dicyclohexyl borane to reduce the diyne to the diene.

Fujimoto et al. in Chem. Pharm. Bull. Japan, 24, 365 (1976) have described the chlorination of unsaturated alcohols using methanesulfonyl chloride as the chlorinating agent in a single step procedure.

The synthesis of internal conjugated (Z)-enynes has been reported in Tetrahedron Letters, No. 7, 633-34 (1979) by G. Cassani, et al.

The stereospecific reduction of a (Z)-ene-yne has been described by a number of prior artisans; see for example E. Truscheit & K. Eiter, Annalen, 1961, 658-65; A. Butenandt, et al., Ibid., 1962, 658, 39; and E. Negishi, et al., J.C.S. Chem. Comm., 1973, 874.

SUMMARY OF THE INVENTION

The invention comprises a process for preparing (Z,Z)-11,13-hexadecadienal, which comprises:

halogenating undecylenic alcohol to obtain 10,11-dihalo-1-undecanol;

dehydrohalogenating the 10,11-dihalo-1-undecanol to obtain 10-undecyn-1-ol;

halogenating the 10-undecyn-1-ol to obtain the 11-halo-1-undecyne;

converting the 11-halo-1-undecyne to the 11-halododecyne Grignard reagent;

complexing the Grignard reagent with acrolein;

hydrolyzing the complex to obtain the 14-halo-1-tetradecen-4-yn-3-ol;

acylating the 14-halo-1-tetradecen-4-yn-3-ol;

reacting the acylate with methylmagnesium bromide in the presence of a catalytic proportion of cuprous ion to obtain a 15-halo-(Z)-3-pentadecen-5-yne;

reducing the 15-halo-(Z)-3-pentadecen-5-yne to obtain 15-halo-(Z,Z)-3,5-pentadecadiene;

converting the 15-halo-(Z,Z)-3,5-pentadecadiene to the (Z,Z)-11,13-hexadecadienal dialkyl acetal; and cleaving the acetal to obtain the (Z,Z)-11,13-hexadecadienal.

The terms "halo" and "halogen" as used throughout the specification and claims are employed in their usual sense as being embracive of chlorine, bromine, iodine and fluorine.

The process of the invention possesses a number of commercially important advantages over prior art processes. First, it introduces the unstable conjugated diene moiety at as late a stage as possible, thereby avoiding complications during purification of intermediates. Second, the process avoids the more generally accepted oxidation techniques for generating the aldehyde function, as these methods are usually unsuitable for large-scale preparations. Thus, the process of the invention lends itself to large-scale manufacture of the (Z,Z) conjugated diene.

The product of the process is a pheromone useful in methods of controlling populations of the navel orange worm.

DETAILED DESCRIPTION OF THE PREFERRED EMBODIMENTS OF THE INVENTION

The process of the invention may be exemplified by the following description of a preferred embodiment process of the invention. The preferred process is conveniently carried out in several, successive steps. The first step (A) is shown schematically in the formulae:

STEP (A)

[I]

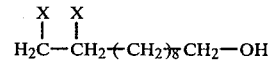

[II]

wherein X represents halogen.

As shown by the above formulae, undecylenic alcohol [I] is halogenated (preferably brominated) in step (A) of the process of the invention to obtain 10,11-dihalo-1-undecanol [II]. The halogenation may be carried out at temperatures below room temperature, advantageously within the range of from about −25° to +25° C., preferably circa 0° C., in the presence of an inert organic solvent for the undecylenic alcohol [I]. The term "inert organic solvent" as used herein means an organic solvent which does not enter into or otherwise adversely affect the desired course of the reaction. Representative of inert solvents which may be used in the step (A) halogenation are the halogenated hydrocarbon solvents. In the preferred process, bromination is generally complete in several hours as indicated by cessation of bromine take-up. Upon completion of the reaction, the desired compound of formula [II] may be separated by stripping the solvent from the reaction mixture.

In the following step (B) of the process of the invention, the 10,11-dihalo-1-undecanol [III] is dehydrohalogenated by reaction with a strong base such as sodamide in liquid ammonia, to obtain the compound 10-undecyn-1-ol [III]. The dehydrohalogenation with sodamide as a representative strong base may be illustrated in the following schematic formulae:

STEP (B)

[II]

[III]

wherein X is as previously defined. The base-initiated elimination reaction progresses advantageously by slow addition of the dihalo reactant [II], dissolved in an inert organic solvent as defined above, to a stoichiometric excess of the sodamide. Representative of solvents advantageously used in the step (B) are tetrahydrofuran and the like. Upon completion of the reaction, the desired 10-undecyn-1-ol [III] separates from the reaction mixture in an organic layer.

In step (C) of the process of the invention, the alcohol [III] is halogenated (preferably chlorinated). Employing methanesulfonyl chloride as the halogenating agent, the step may be illustrated by the following reaction scheme:

STEP (C)

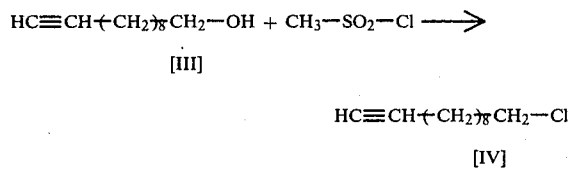

As shown in the formulae, the 10-undecyn-1-ol of formula [III] is halogenated in step (C) to obtain the corresponding 11-halo-1-undecyne. Alternatively, thionyl chloride or the like may be used as a preferred chlorination agent. The halogenation illustrated above may be carried out following the general procedure of Y. Fujimoto, et al., Chem. Pharm. Bull. Japan, 24, 365 (1976). In general, the halogenation is advantageously carried out at room temperatures or slightly below, up to about 100° C. in the presence of an inert organic solvent as previously defined. Representative of preferred solvents are dimethylformamide and the like. The reaction mixture also advantageously contains an acid acceptor (binding agent) such as a tertiary amine. Illustrative of tertiary amines which may be used are quinoline, trimethylamine, triethylamine, pyridine and the like. The reaction is generally complete within about 12 hours and may be followed using conventional analytical techniques. The desired product compound such as the chloride of formula [IV] may be separated from the reaction mixture by conventional techniques such as by extraction in a solvent, distillation and like procedures.

The next step, i.e.; Step (D) in the process of the invention may be illustrated in the schematic formulae:

STEP (D)

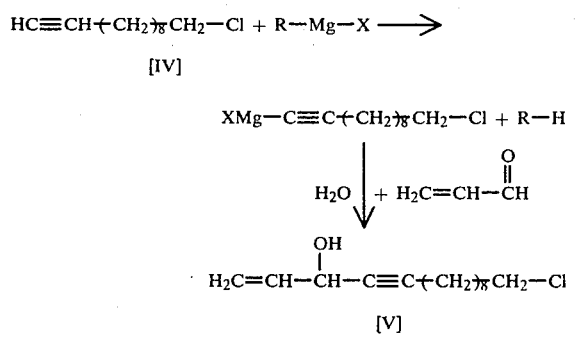

wherein X has the meaning previously given to it and R represents hydrocarbyl. The term "hydrocarbyl" as used herein means the monovalent moiety obtained upon removal of a hydrogen atom from a parent hydrocarbon. Representative of hydrocarbyl are alkyl of 1 to 12 carbon atoms, inclusive, such as methyl, ethyl, propyl, butyl, pentyl, hexyl, heptyl, octyl, nonyl, decyl, undecyl, dodecyl and isomeric forms thereof; cycloalkyl of 3 to 6 carbon atoms, inclusive, such as cyclopropyl, cyclobutyl, cyclopentyl and cyclohexyl; aryl of 6 to 10 carbon atoms, inclusive, such as phenyl and napthyl. Preferably, R is lower alkyl (1 to 3 carbons).

As shown in the above reaction scheme, the chloride (or analog halide) of formula [IV] is converted to the homolog corresponding Grignard reagent by reaction with a hydrocarbyl magnesium halide (Grignard reagent) such as ethylmagnesium bromide in Step (D) of the process of the invention, followed immediately by complexing of the Grignard reaction product with acrolein. The reaction and formation of the Grignard complex is advantageously carried out in the presence of an inert organic solvent as previously defined, such as ethyl ether, tetrahydrofuran and the like. The reaction with the ethyl magnesium bromide or like Grignard reagent is preferably carried out at a temperature of about reflux for the reaction mixture. The following complexing reaction is preferably carried out at a temperature within the range of from about 15° to about 30° C. The progress of each of the reactions may be followed by conventional analytical techniques. When complete, the Grignard complex reaction product may be hydrolyzed and the corresponding alcohol product, as represented by 14-chloro-1-tetradecen-4-yn-3-ol (formula [V]), separated by conventional extraction and distillation techniques.

In step (E) of the preferred process of the invention, the compound of formula [V] is acylated, to obtain the 14-halo-1-tetradecen-4-yn-3 acylate of formula [VI]. The acylation may be illustrated with the following schematic formulae:

STEP (E)

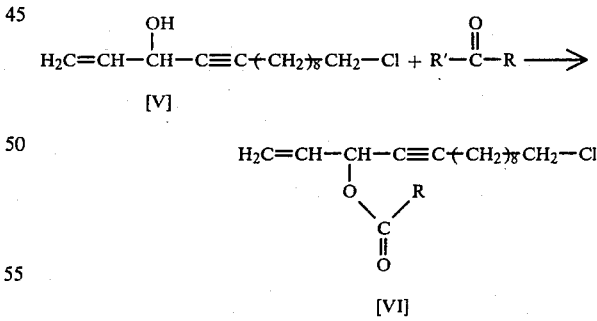

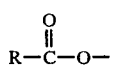

wherein R is as previously defined and R' represents one of a halogen, a hydroxyl group or a group of the formula:

$$R-\overset{O}{\underset{\|}{C}}-O-$$

wherein R has the meaning previously ascribed to it.

In the acylation shown above, the acylating agent of formula:

contributes the acyl radical of formula;

as a moiety in the acylate of formula [VI]. Preferably, the acyl radical is a carboxylic acid acyl radical, advantageously a hydrocarbon carboxylic acid acyl of not more than 18 carbon atoms; or halo-, nitro-, hydroxy-, amino-, cyano-, thiocyano-, or lower alkoxy-substituted hydrocarbon carboxylic acid acyl radical advantageously of not more than 18 carbon atoms. Representative of carboxylic acid acyl radicals are the acyl radicals of the following acids:

(a) saturated or unsaturated, straight or branched chain aliphatic carboxylic acids, for example acetic, propionic, butyric, isobutyric, tert-butylacetic, valeric, isovaleric, caproic, caprylic, succinic, decanoic, dodecanoic, lauric, tridecanoic, myristic, pentadecanoic, palmitic, margaric, stearic, acrylic, crotonic, undecylenic, oleic, hexynoic, heptynoic, octynoic, acids, and the like;

(b) saturated or unsaturated, alicyclic carboxylic acids, for example, cyclobutanecarboxylic acid, cyclopentanecarboxylic acid, methylcyclopentenecarboxylic acid, cyclohexanecarboxylic acid, dimethylcyclohexenecarboxylic acid, dipropylcyclohexanecarboxylic acid, and the like;

(c) saturated or unsaturated, alicyclic aliphatic carboxylic acids, for example cyclopentanepropionic acid cyclohexanebutyric acid, methylcyclohexaneacetic acid, and the like, (d) aromatic carboxylic acids, for example, benzoic acid, toluic acid, naphthoic acid, ethylbenzoic acid, isobutylbenzoic acid, methylbutylbenzoic acid, and the like; and (e) aromaticaliphatic carboxylic acids, for example, phenylacetic acid, phenylpropionic acid, phenylvaleric acid, cinnamic acid, phenylpropionic acid and naphthylacetic acid, and the like. Suitable halo-, hydroxy-, amino-, cyano-, thio-, cyano-, and lower alkoxyhydrocarbon carboxylic acids include hydrocarbon carboxylic acids as given above which are substituted by one or more of halogen, nitro, hydroxy, amino, cyano, or thiocyano, or loweralkoxy, advantageously loweralkoxy of not more than 18 carbon atoms, for example, methoxy, ethoxy, propoxy, butoxy, amyloxy, hexyloxy, and isometric forms thereof. Examples of such substituted hydrocarbon carboxylic acids are mono-di-, and trichloroacetic acid;
and -chloropropionic acid
and -bromobutyric acid;
and -iodovaleric acid;
mevalonic acid;
2-and 4-chlorocyclohexanecarboxylic acid;
shikimic acid;
2-nitro-1-methyl-cyclobutanecarboxylic acid;
1,2,3,4,5,6-hexachlorocyclohexanecarboxylic acid;
3-bromo-2-methylcyclohexanecarboxylic acid;
4-and 5-bromo-2-methylcyclohexanecarboxylic acid;
6-bromo-2-methylcyclohexanecarboxylic acid;
2,3-dibromo-2-methyl-cyclohexanecarboxylic acid;
2,5-dibromo-2-methylcyclohexanecarboxylic acid;
4,5-dibromo-2-methylcyclohexanecarboxylic acid;
5,6-dibromo-2-methylcyclohexanecarboxylic acid;
3-bromo-3-methylcyclohexanecarboxylic acid;
6-bromo-3-methylcyclohexanecarboxylic acid;
1,6-dibromo-3-methylcyclohexanecarboxylic acid;
2-bromo-4-methylcyclohexanecarboxylic acid;
1,2-dibromo-4-methylcyclohexanecarboxylic acid;
3-bromo-2,2,3-trimethylcyclopentanecarboxylic acid;
1-bromo-3,5-dimethylcyclohexanecarboxylic acid;
homogentisic acid, o-, m-, and p-chlorobenzoic acid;
anisic acid;
salicylic acid;
p-hydroxybenzoic acid;
beta-resorcylcic acid;
gallic acid;
veratric acid;
trimethoxybenzoic acid;
trimethoxycinnamic acid;
4,4'-dichlorobenzilic acid;
o-, m-, and p-nitrobenzoic acid;
cyanoacetic acid;
3,4-and 3,5-dinitrobenzoic acid;
2,4,6-trinitrobenzoic acid;
thiocyanoacetic acid;
cyanopropionic acid;
lactic acid;
ethoxyformic acid(ethyl hydrogen carbonate);
butoxyformic acid;
pentyloxyformic acid;
hexyloxyformic acid;
dodecyloxyformic acid;
hexadecyloxyformic acid; and the like.

Alternatively the acid anhydrides, where available, may be used to acylate the compounds of formula [V], preferably acetic anhydride. Preferably a stoichiometric excess of the anhydride is reacted with the compound [V].

The acylation is advantageously carried out by admixture of the acylating agent with the compound [V] in the presence of an acid binding agent, for example a tertiary amine. Illustrative of tertiary amines which may be used are pyridine, quinoline, trimethylamine, triethylamine and the like. Advantageously the acylation is carried out in the presence of an inert solvent, i.e.; a solvent for the acylating agent which does not interfere with or alter the desired course of the acylation. Representative of such inert solvents are chloroform, ether, dimethyl formamide and the like. The acylation proceeds at room temperatures and may be followed by conventional analytical techniques. Upon completion of the acylation, the desired acylate may be separated from the reaction mixture by conventional techniques such as by distillation and like techniques.

In step (F) of the above schematic formulae, the acylate such as the acetate of formula [VI] is coupled with methylmagnesium halide in the presence of a catalytic proportion of cuprous ion to obtain the rearranged 15-chloro-(Z)-3-pentadecen-5-yne of the formula [VII]. Sources of the cuprous ion are preferably from compounds of the formula:

wherein Y represents halogen or cyanide. The general procedure may be that described by Cassani et al., Tet. Lett., No. 7, 633–34 (1979) employing dilithium tetrachlorocuprate as the preferred source of cuprous ion catalyst. The reaction may be illustrated by the schematic formulae:

STEP (F)

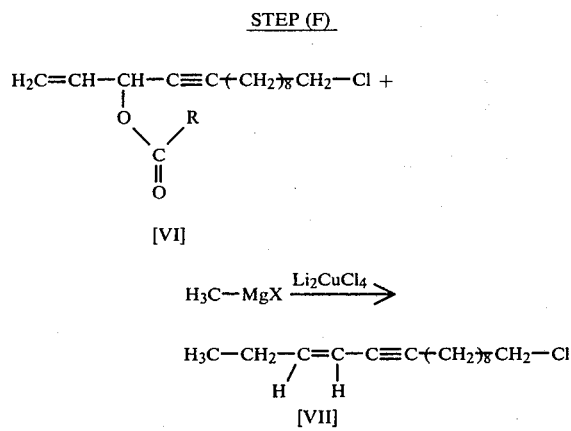

As will be observed, the methyl group from the Grignard reagent is coupled in the cis fashion, probably through an organo copper intermediate. Advantageously the reaction is carried out in the presence of an inert organic solvent as previously defined, such as tetrahydrofuran and the like. Also advantageously the reaction is carried out at a temperature of less than about $-30°$ C., most preferably circa $-35°$ C. It is worth noting that this reaction proved to be highly stereospecific, producing ene-yne of nearly 99% (Z) configuration, with 15% of by-products from side reactions and direct attack on the carbonyl function. Compound [VII] is a novel intermediate compound which also proved to be very stable thermally and to be unusually resistant to isomerization.

The desired compound of formula [VII] may be conveniently separated from the reaction mixture by conventional techniques such as by distillation.

The following step (G) of the process of the invention may be illustrated with the schematic formulae:

STEP (G)

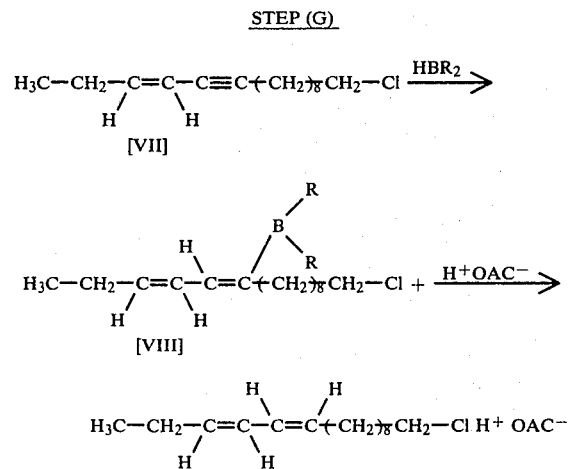

In step (G) of the process of the invention, the compound [VII] is selectively treated to reduce the 5-yne bond. Advantageously, selective stereospecific reduction occurs when the compound of formula [VII] is reduced, preferably by monohydroboration with a boron hydride, followed by protonolysis of the product borane with acetic acid. Preferred boron hydrides for the hydroboration are those of the formulae:

wherein each R is as defined above, i.e., hydrocarbyl. Most preferred as the boron hydride is one where each R is alkyl or cycloalkyl, most preferably dicyclohexyl borane. The preferred reduction may be carried out at a temperature of from about $-20°$ C. to room temperature to obtain the compound of formula [VIII] which is 15-chloro-(Z,Z)-3,5-pentadecadiene. The progress of the reaction may be followed by conventional analytical procedures and the product [VIII] separated from the reaction mixture by conventional techniques such as by extraction, distillation and like procedures. Preferably the product compound of formula [VIII] is purified by urea clathration in step (H). In the step (H), the product (Z,Z) conjugated diene is separated from isomeric forms thereof through selective formation of the (Z,Z) isomer clathrate (inclusion complex with urea or thiourea). The clathrate forms by simple admixture of the (Z,Z) isomer of the conjugated diene with urea or thiourea in an inert solvent as defined above, for the isomer and the urea or thiourea. Representative of such solvents are methanol, ethanol, propanol, dimethylformamide and like polar organic solvents. The clathrate formed is in the form of a crystalline precipitate which may be separated from the reaction mixture by decantation, filtration and like techniques. The separated clathrate may then be dissolved in water and the resulting mixture extracted with a water-immiscible organic solvent for the (Z,Z) isomer such as n-hexane and the like. Separation of the organic extract layer and concentration of the conjugated diene from the extract gives a very pure yield of the desired (Z,Z) isomer of the formula VIII. It has not, to our knowledge, been previously reported that (Z,Z) conjugated dienes form urea complexes in preference to related geometric isomers.

Following urea clathration, the compound of formula [VIII] is converted to the Grignard reagent and the latter reacted with a trihydrocarbyl orthoformate in an acetal exchange to give the (Z,Z)-11,13-hexadecadienal dihydrocarbyl acetal of the formula [IX] as shown schematically below in the Step (I).

STEP (I)

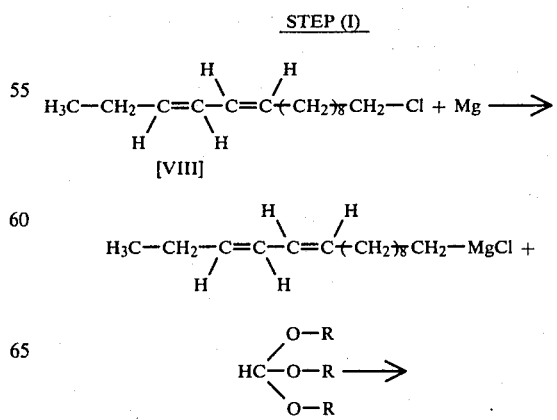

-continued
STEP (I)

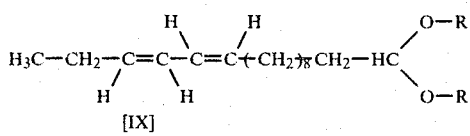

wherein each R has the meaning ascribed to it previously and is independently selected. The moiety R in the formulae of Step (I) is preferably lower alkyl. The exchange reaction with the trihydrocarbyl orthoformate is advantageously carried out in an inert organic solvent as previously defined, such as tetrahydrofuran, at reflux temperatures. Progress of the reaction may be followed by standard analytical procedures. Upon completion of the reaction, separation of this heat-sensitive compound of the formula [IX] may be effected by means of using a thin-film evaporator whereby distilled acetal is obtained with a minimum of isomerization of the diene functionality.

Finally, cleavage of the acetal [IX] with acid yields in Step (J) the desired (Z,Z)-11,13-hexadecadienal of formula [X] as a clear, pale yellow liquid which is of sufficient purity and quality as to require no further purification. The cleavage may be illustrated in the schematic formulae:

STEP (J)

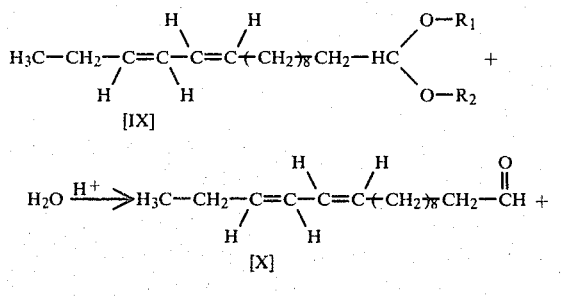

The following example describes the manner and the process of making the invention and sets forth the best mode contemplated by the inventors for carrying out the invention.

EXAMPLE (A). Preparation of 10,11-dibromo-1-undecanol 34 kg. (200 moles) of undecylenic alcohol is dissolved in 200 l of dichloromethane and cooled to a temperature of −5° C. after which liquid bromine is added over a four hour period while maintaining the temperature at 0° to −5° C. After the addition, the reaction mixture is stirred an additional four hours, then the solvent is stripped under vacuum (pot temperature of not more than 50° C.). The crude dibromide product is used directly in the next step without further purification. The yield is essentially quantitative.

(B). Preparation of 10-undecyn-1-ol

The crude dibromide from Step (A), supra., is divided into 13 parts to facilitate handling in a 50 l liquid ammonia reactor. In each run, 18 l of liquid ammonia is added to 3120 gr. (65 moles) of sodamide. After 5 minutes of stirring, 6.1 kg. (18.5 moles) of the dibromide is dissolved in 3.5 l of tetrahydrofuran and added over a period of about one hour to the reaction mixture. The resulting mixture is stirred an additional 16 hours, then quenched with 2.27 kg. of powdered ammonium chloride followed by 24 l of water. After separation of the resulting layers the crude alcohol is washed four times with a half-volume of brine, then flash distilled off a small amount of butylated hydroxy toluene (BHT) at 120° C./1 mm Hg to yield (after combining of the 13 runs as above) 26.17 kg. (155.8 moles) of 10-undecyn-1-ol (yield based on undecylenic alcohol is 78%).

(C). Preparation of 11-chloro-1-undecyne 155.8 moles of 10-undecyn-1-ol from Step (B), supra., is charged to a reactor along with 161.5 lbs. of dimethylformamide and 29.8 lbs. of pyridine. To this stirred mixture there is added methanesulfonyl chloride at such a rate so as to maintain the temperature of the reaction mixture at 20°–25° C. (cooling is necessary). The mixture is stirred an additional hour at this temperature then slowly heated to 75°–85° C. and held there for twelve hours. After this period of time a sample is pulled, washed several times and dried over sodium sulfate. A gas chromatographic analysis on a 6' carbowax column shows no remaining alcohol or its corresponding mesylate. A spike with authentic 11-chloro-1-undecyne shows this to be the only major product present. The reaction mixture is cooled to about 50° C. and 50 gallons of water is quickly added along with 7 gallons of hexane. After standing, the lower (aqueous) phase is discarded and the hexane/product layer washed twice with 15 gallons of brine. After stripping off the hexane at atmospheric pressure to azeotropically dry the product, it is flash distilled at 100° C./3 mm Hg, then redistilled on a metal packed column of about 30 plates efficiency to yield 18 kg. (96.5 moles) of 95% pure 11-chloro-1-undecyne (yield from alcohol is 62%).

(D). Preparaton of 14-chloro-1-tetradecen-4-yn-3-ol

To 101 moles of 2.0 M ethylmagnesium bromide there is added neat 11-chloro-1-undecyne (18 kg., 96.5 moles) at the reflux temperature of tetrahydrofuran. An immediate evolution of ethane ensues. After the addition, the reaction mixture is stirred at reflux for several additional hours, then cooled under nitrogen gas to about 30° C. Next, a mixture of 5.3 kg. of acrolien (94.4 moles) dissolved in 12 l of tetrahydrofuran is added over a two hour period, while keeping the temperature below 30° C. After stirring an additional 12 hours, a sample is pulled, hydrolyzed and analyzed by gas chromatography on a 6' carbowax column. Typical runs show about 20% unreacted chloro undecyne (recoverable) with the remainder being 14-chloro-1-tetradecen-4-yn-3-ol as evidenced by spiking with authentic material. The reaction mixture is then cooled to a temperature of 10° C. and hydrolyzed with a mixture of 9 l of water and 9 l of acetic acid. Hexane is added (9 l) and the crude product washed three times with a half-volume of brine, then stripped under vacuum (pot temperature of about 95° C. at 2 mm Hg.). Then 13 kg. of crude alcohol is isolated and used directly in the next Step (E) after checking the material for dryness by Karl Fischer titration [dryness advantageously is about 0.05% water or less before proceeding on to Step (E)].

(E). Preparation of 14-chloro-1-tetradecen-4-yn-3-ol acetate

To the crude alcohol from Step (D) supra., there is added 2.34 kg. (29.6 moles) of dry pyridine. Under a blanket of nitrogen gas, 6 kg. (59.2 moles) of acetic anhydride is added at room temperature over a 6 hour period. After stirring several additional hours, a sample is pulled and analyzed on a 6' carbowax column for loss of alcohol and appearance of the desired acetate. After completion of the reaction, the crude product is transferred to a distillation apparatus where the excess acetic anhydride and residual pyridine are removed under vacuum. Finally, the product is flash distilled through a thin film evaporator, the first pass removing residual lights and unreacted 11-chloro-1-undecyne from Step (D), supra., and the second pass to flash the product off higher boiling residues at 170° C./3 mm Hg. This yields 15.3 kg. (53.8 moles) of the acetate which is sufficiently pure to carry on to the next step (yield is 55.7% based on 11-chloro-1-undecyne in Step (D) supra.).

(F). Preparation of 15-chloro-(Z)-3-pentadecen-5-yne

A solution of 57.9 moles of 1.5 M methylmagnesium bromide in tetrahydrofuran is prepared, then stored at 50° C. under nitrogen gas. A solution of 14-chloro-1-tetradecen-4-yn-3-01 acetate (15.3 kg. or 53.8 moles) in 17.5 l of tetrahydrofuran is placed in a reaction vessel along with 17 l of standard dilithium tetrachlorocuprate solution (made by dissolving 13.5 gr. of cuprous chloride and 8.5 gr. of lithium chloride in one liter of tetrahydrofuran to obtain one liter of standard solution) and cooled to −30° C. under nitrogen gas. To this cooled, stirred solution the previously prepared methylmagnesium bromide solution is added over a four hour period, keeping the temperature at −30° C. The reaction mixture is stirred an additional half-hour at −30° C. then allowed to warm to room temperature over several hours. A sample is then pulled and hydrolyzed with acetic acid/water and checked by gas chromatography on a 6' carbowax column which reveals the absence of any starting acetate and a cluster of one major and three minor peaks, the major being the desired 15-chloro-(Z)-3-pentadecen-5-yne as previously identified by nuclear magnetic resonance spectroscopy. Keeping the reaction mixture below a temperature of 25° C., a solution of 5 l of acetic acid in 6 l of water is added, after which the layers are separated and the organic layer washed twice with a half-volume of brine. After vacuum stripping of residual tetrahydrofuran, the product is flash distilled off heavies at 130° C./1 mm Hg, then redistilled on a 2" by 4' metal packed column to effect separation of the desired product from close boiling impurities (yielding 5.8 kg. 24.1 moles of 99% 15-chloro-(Z)-3-pentadecen-5-yne, containing less than 1% (E) isomer; by glass capillary gas chromatography). Yield from starting acetate is 44.8% (theoretical).

(G). Preparation of 15-chloro-(Z,Z)-3,5-pentadecadiene

The chloride from Step (F) supra., is divided into four approximately equal parts to facilitate handling. Each run is as follows. To 7 moles of 1.0 M borane tetrahydrofuran (THF) complex is added 1262 gr. (15.4 moles) of cyclohexene (at 2°-10° C.) over a two hour period, after which the resulting dicyclohexyl borane suspension is stirred an additional four hours at 5°-10° C. In another reaction vessel there is placed 1.5 kg. of 15-chloro-(Z)-3-pentadecen-5-yne in 1750 mls of dry tetrahydrofuran cooled to −10° C. under nitrogen gas. The previously prepared dicyclohexyl borane/THF suspension is slowly added to the ene-yne/THF solution at a temperature of −10° C. over a two hour period after which the reaction mix is allowed to warm to room temperature and stirred an additional 12 hours to obtain a monohydroborane intermediate compound. Protonolysis of a sample with an equal volume of acetic acid at 50° C. for a half-hour followed by several brine washes, then analysis on a 6' carbowax column shows less than 0.5% unreacted ene-yne plus about 2% mono-olefinic product. Next, 1565 mls of acetic acid is added to the reaction mixture over a one hour period at a temperature of 30° C., after which the temperature is raised to 55° C. and maintained for an additional 5 hours to insure completion of protonolysis. After cooling the reaction mixture to 5° C., 5240 mls of 6 N sodium hydroxide solution is added quickly with a resultant exotherm to 25° C. Keeping the temperature at 30° C., 1040 mls of 47% hydrogen peroxide is added slowly over a two hour period followed by 15 minutes of additional stirring. Next, 1 gallon of hexane is added to assist in the layer separation. The lower (aqueous) phase is discarded and the product/THF/hexane layer washed five times with a half-volume of brine, followed by vacuum stripping of the solvents (keeping the pot temperature below 50° C.). The crude 15-chloro-(Z,Z)-3,5-pentadecadiene thus obtained is ready for purification by urea clathration to remove by-product cyclohexanol and residual boron compounds.

(H). Isolation of 15-chloro-(Z,Z)-3,5-pentadecadiene

The crude chlorodiene product from Step (G) supra., is divided into several parts and each treated as follows. To 9000 mls of methanol is added 4450 gr. of urea and the resulting slurry is stirred and heated to 60° C. After the urea is dissolved, 1277 gr. of the crude chlorodiene (containing about 500 gr. of cyclohexanol) is added quickly, whereupon a fine, white precipitate immediately begins to form. This slurry is stirred and slowly cooled to a temperature of 25° C. overnight, then filtered through a Buchner funnel. The cake is washed twice with 1 l of hexane, sucked dry, then added to 12 l of hot water with stirring. After adding 1 l of hexane to the stirred mixture, the layers are allowed to separate and the water layer discarded. The organic layer is washed twice with a half-volume of brine, then vacuum stripped at 50° C. to 1 mm Hg. In this way, after combining several runs, clear, dry, water white, 15-chloro-(Z,Z)-3,5-pentadecadiene (4.6 kg. or 19 moles) is obtained which is sufficiently pure to carry on to the following Grignard preparation [yield is 79% overall from ene-yne in Step (G)].

(I). Preparation of (Z,Z)-11,13-hexadecadienal diethyl acetal

The Grignard reagent of the chlorodiene from Step (H) Supra., is prepared in a 3-necked flask equipped with a stirrer, a thermometer, a reflux condenser, addition funnel and a nitrogen purge means. To the flask there is charged 500 gms. of magnesium (20.6 moles). The magnesium is covered with tetrahydrofuron (THF) and an aliquot of chlorodiene charged neat. The reaction is initiated with gentle heating and stirring. At this point chlorodiene (4.6 Kg, 19 moles) in THF (10 l) is added at a rate sufficient to maintain reflux without the need of applying external heat. Following the completion of addition, the reaction mixture is refluxed for 4 hours (external heat applied). Next, 2.8 kg. (19 moles) of triethyl orthoformate (TEOF) is added slowly while removing (by means of a distillation head) enough THF to raise the reaction temperature to 95° C. When all of the TEOF is added, the reaction mixture is stirred at 95° C. for 48 hours after which a sample is pulled, hydrolyzed, then analyzed on a 6' carbowax column. The reaction is considered complete when the ratio of product to pentadecadiene (product of hydrolysis of the unreacted Grignard reagent) is about 7.5 to 1. Next, the reaction mixture is cooled to 30° C. and hydrolyzed with 1700 mls of water after which the organic layer is decanted from the resulting magnesium salts (which are subsequently washed three times with 1 l of THF). Finally, the magnesium salts are dissolved with 6 l of water and 2.5 l of acetic acid, keeping the temperature below 20° C. to avoid hydrolysis of any remaining acetal. The aqueous phase is discarded, the small organic layer washed three times with a half-volume of brine and once with a half-volume of dilute sodium carbonate soltuion until basic. The combined organic layers are vacuum stripped to a pot temperature of 50° C. at 1 mm Hg. The resulting crude acetal is now flash distilled through a 2" Pope thin film evaporator. The first pass at 135°–140° C. at 0.5 mm Hg. removes the lower boiling hydrocarbon by-product [(Z,Z)-3,5-pentadecadiene] containing around 20% acetal in the distillate. The resulting crude acetal contains less than 2% hydrocarbon impurity and is passed through again to flash the product off high boiling residue at 175°–180° C. at 0.5 mm Hg. The thick residue is found to contain less than 5% acetal after pass two. The distillate from pass one is redistilled at 150° C./0.5 mm Hg. to concentrate the contained acetal which, after this pass, again contains less than 2% hydrocarbon impurity. In this way, 3.8 kg. (12.26 moles) of (Z,Z)-11,13-hexadecadienal diethyl acetal is obtained at an overall purity of 95.7% (not including isomeric impurities) containing 1.27% (Z,Z)-3,5-pentadecadiene and 2.35% of an impurity believed to be mono-olefinic acetal. The distilled product is carried on to the next Step (J) without further treatment. Yield based on chlorodiene is 64.5%.

(J). Preparation of (Z,Z)-11,13-hexadecadienal

The distilled acetal from Step (I) supra., is placed in a reaction flask along with 36.8 moles (1.7 kg.) of 90% formic acid and heated with vigorous stirring to a pot temperature of 75° C. until a reflux of ethyl formate ensues. By means of a distillation head, the refluxing ethyl formate is removed until the pot temperature rises to 95° C. At this point, the ethyl formate ceases to distill from the reaction mixture and stirring is continued for 15 minutes more at this temperature after which cooling is applied to bring the contents of the flask to a temperature of about 35° C. The residual excess formic acid is separated and discarded and the neat aldehyde washed three times with a half-volume of brine. Finally, the product is placed in a stirred, heated flask and vacuum is applied to remove residual water and ethyl formate (pot temperature of 50° C. at 1 mm Hg.). The resulting pale yellow aldehyde is filtered through a glass wool plug to remove any suspended fines and stored in aluminum bottles. Analysis of a sample on a 20 meter CC-52 glass capillary column at 195° C. gives the following results; contained (Z,Z)-11,13-hexadecadienal, 90.0%, with 3.53% (Z,E) isomer and 2.24% (E,Z) isomer with less than 0.5% (E,E) isomer (plus the aforementioned 1.27% hydrocarbon and 2.35% monoolefinic impurities). Subsequent analysis by infra-red spectroscopy shows the spectrum to be identical to that of authentic material. Thus, 2.8 kg. of (Z,Z)-11,13-hexadecadienal is obtained (yield of 97% from the diethyl acetal).

What is claimed is:

1. A process for preparing (Z,Z)-11,13-hexadecadienal, which comprises;
    halogenating undecylenic alcohol at a temperature below room temperature to obtain 10,11-dihalo-1-undecanol;
    dehydrohalogenating the 10,11-dihalo-1-undecanol by reaction with a strong base to obtain 10-undecyn-1-ol;
    chlorinating the 10-undecyn-1-ol to obtain 11-chloro-1-undecyne;
    converting the 11-chloro-1-undecyne to the 11-chlorododecyne Grignard reagent;
    complexing the Grignard reagent with acrolein at a temperature of from about 15° to about 30° C.;
    hydrolyzing the complex to obtain 14-chloro-1-tetradecen-4-yn-3-ol;
    acylating the 14-chloro-1-tetradecen-4-yn-3-ol with an acyl radical of the formula

wherein R represents hydrocarbyl;
    reacting the acylate with methylmagnesium bromide in the presence of a catalytic proportion of cuprous ion to obtain 15-chloro-(Z)-3-pentadecen-5-yne at a temperature of less than about −30° C.;
    reducing the 15-chloro-(Z)-3-pentadecen-5-yne to 15-chloro-(Z,Z)-3,5-pentadecadiene at a temperature of from about −20° C. to room temperature by hydroboration of the 15-chloro-(Z)-3-pentadecen-5-yne followed by protonolysis of the product borane;
    converting the 15-chloro-(Z,Z)-3,5-pentadecadiene to the (Z,Z)-11,13-hexadecadienal dialkyl acetal by reaction with a compound of the formula

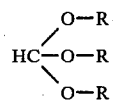

wherein R is as previously defined; and
    cleaving the acetal to obtain the (Z,Z)-11,13-hexadecadienal by acid hydrolysis of the acetal.

2. The process of claim 1 wherein the cuprous ion is provided by dilithium tetrachlorocuprate.

3. A process for preparing (Z,Z)-11,13-hexadecadienal, which comprises;
    brominating undecylenic alcohol at a temperature below room temperature to obtain 10,11-dibromo-1-undecanol;
    dehydrobrominating the 10,11-dibromo-1-undecanol by reaction with a strong base to obtain 10-undecyn-1-ol;
    chlorinating the 10-undecyn-1-ol to obtain the 11-chloro-1-undecyne;
    converting the 11-chloro-1-undecyne to a Grignard reagent and complexing the Grignard reaction product with acrolein at a temperature of from about 15° to about 30° C.

hydrolyzing the complex to obtain 14-chloro-1-tetradecen-1-yn-3-ol;

acylating the 14-chloro-1-tetradecen-4-yn-3-ol with acetic anhydride to obtain the 14-chloro-1-tetradecen-4-yn-3-acetate;

reacting said acylate with methylmagnesium bromide at a temperature of less than about −30° C. in the presence of a catalytic proportion of dilithium tetrachlorocuprate to obtain 15-chloro-(Z)-3-pentadecen-5-yne;

reducing the 15-chloro-(Z)-3-pentadecen-5-yne with dicyclohexyl borane followed by protonolysis of the product borane with acetic acid to obtain 15-chloro-(Z,Z)-3,5-pentadecadiene;

converting the 15-chloro-(Z,Z)-3,5-pentadecadiene to the corresponding (Z,Z)-11,13-hexadecadienal diethyl acetal by reaction with triethyl orthoformate; and cleaving the acetal to obtain the (Z,Z)-11,13-hexadecadienal, by acid hydrolysis of the acetal.

* * * * *

UNITED STATES PATENT AND TRADEMARK OFFICE
CERTIFICATE OF CORRECTION

PATENT NO. : 4,400,550
DATED : August 23, 1983
INVENTOR(S) : Clyde E. Bishop et al It is certified that error appears in the above-identified patent and that said Letters Patent is hereby corrected as shown below:

At Col. 9, line 6; at the end of the line " 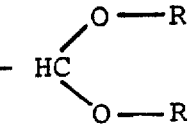 "

should read --  --

At Col. 9, line 33; at the end of the line " — HC(O—R₁)(O—R₂) + "

should read -- —C(O—R₁)(H)(O—R₂) + --

Signed and Sealed this

Twentieth Day of December 1983

[SEAL]

Attest:

GERALD J. MOSSINGHOFF

*Attesting Officer*    *Commissioner of Patents and Trademarks*